(12) United States Patent
Hyun et al.

(10) Patent No.: US 11,437,013 B2
(45) Date of Patent: Sep. 6, 2022

(54) ULTRA-THIN ACOUSTIC LENS FOR SUBWAVELENGTH FOCUSING IN MEGASONIC RANGE, AND DESIGN METHOD THEREFOR

(71) Applicant: Korea Research Institute of Standard and Science, Daejeon (KR)

(72) Inventors: Jae-yub Hyun, Jeollabuk-do (KR); Yong-tae Kim, Daejeon (KR); Il Doh, Daejeon (KR); Bong-young Ahn, Daejeon (KR); Kyung-min Baik, Daejeon (KR); Se-hwa Kim, Daejeon (KR)

(73) Assignee: Korea Research Institute of Standard and Science, Daejeon (KR)

( * ) Notice: Subject to any disclaimer, the term of this patent is extended or adjusted under 35 U.S.C. 154(b) by 0 days.

(21) Appl. No.: 16/977,782

(22) PCT Filed: May 30, 2018

(86) PCT No.: PCT/KR2018/006128
§ 371 (c)(1),
(2) Date: Sep. 2, 2020

(87) PCT Pub. No.: WO2019/231009
PCT Pub. Date: Dec. 5, 2019

(65) Prior Publication Data
US 2021/0366458 A1 Nov. 25, 2021

(51) Int. Cl.
*G10K 11/30* (2006.01)
*A61B 8/00* (2006.01)
*A61N 7/00* (2006.01)

(52) U.S. Cl.
CPC ............ *G10K 11/30* (2013.01); *A61B 8/4483* (2013.01); *A61N 2007/006* (2013.01)

(58) Field of Classification Search
None
See application file for complete search history.

(56) References Cited

U.S. PATENT DOCUMENTS

| 6,136,210 A | * | 10/2000 | Biegelsen | B41J 2/14008 |
| | | | | 216/26 |
| 8,616,329 B1 | * | 12/2013 | Welter | G10K 11/30 |
| | | | | 181/176 |
| 9,711,132 B1 | * | 7/2017 | Kim | G01S 7/521 |

FOREIGN PATENT DOCUMENTS

| JP | S6097251 A | 5/1985 |
| KR | 20030082303 A | 10/2003 |

(Continued)

OTHER PUBLICATIONS

Minin, 3D high-Quality Ultrasonic Imaging, Ultrasound Imaging—Medical Applications, 25-38 (Year: 2011).*

(Continued)

*Primary Examiner* — James R Hulka
*Assistant Examiner* — Vikas Atmakuri
(74) *Attorney, Agent, or Firm* — Akerman LLP

(57) ABSTRACT

The present invention relates to an ultra-thin acoustic lens for subwavelength focusing in a megasonic range and a design method thereof. More particularly, the present invention relates to a super-oscillatory planar ultra-thin acoustic lens for subwavelength focusing in the megasonic range, which includes a plurality of concentric regions arranged in a concentric shape with reference to the center point, wherein the concentric regions include a plurality acoustic insulation region for insulating incident acoustic waves, and a plurality of transmission regions for transmitting acoustic waves, the acoustic insulation regions and the transmission regions being formed alternatively in a radial direction from the center point so as to focus incident acoustic wave energy onto a subwavelength region. The acoustic lens has flat (Continued)

surfaces on both sides thereof respectively and has a plate shape having a constant thickness, and a layout, which is a radius of each of the plurality of acoustic insulation regions and transmission regions in the concentric region, is determined by a topology optimization reverse design method.

13 Claims, 13 Drawing Sheets

(56) References Cited

FOREIGN PATENT DOCUMENTS

| KR | 101656185 B1 | 9/2016 |
|---|---|---|
| KR | 20180037349 A | 4/2018 |

OTHER PUBLICATIONS

International Search Report issued in connection with PCT/KR2018/006128.

* cited by examiner

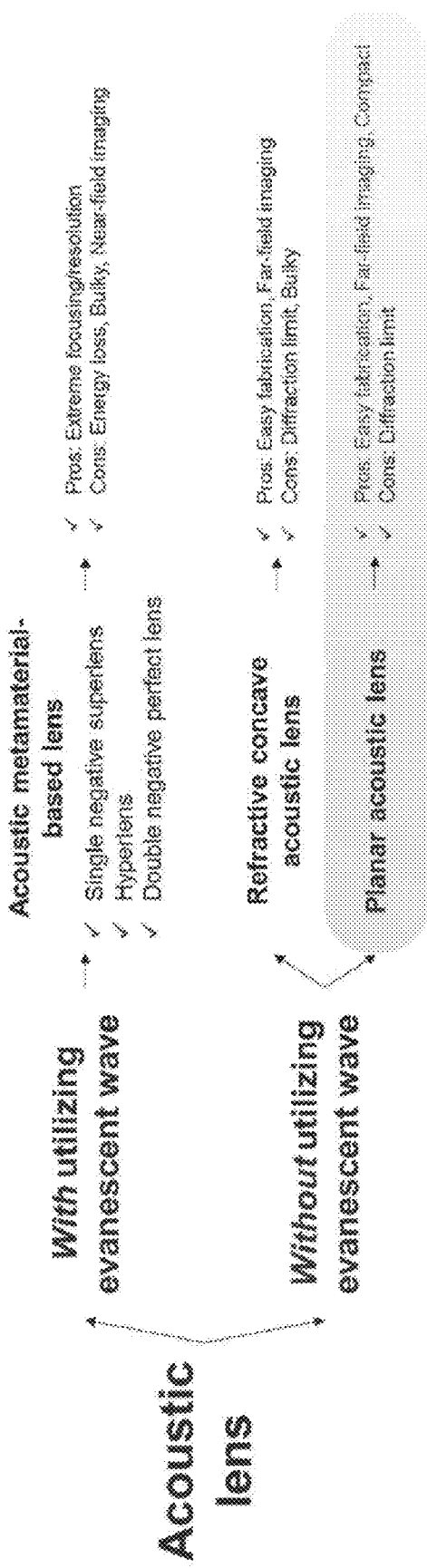
[FIG. 1]

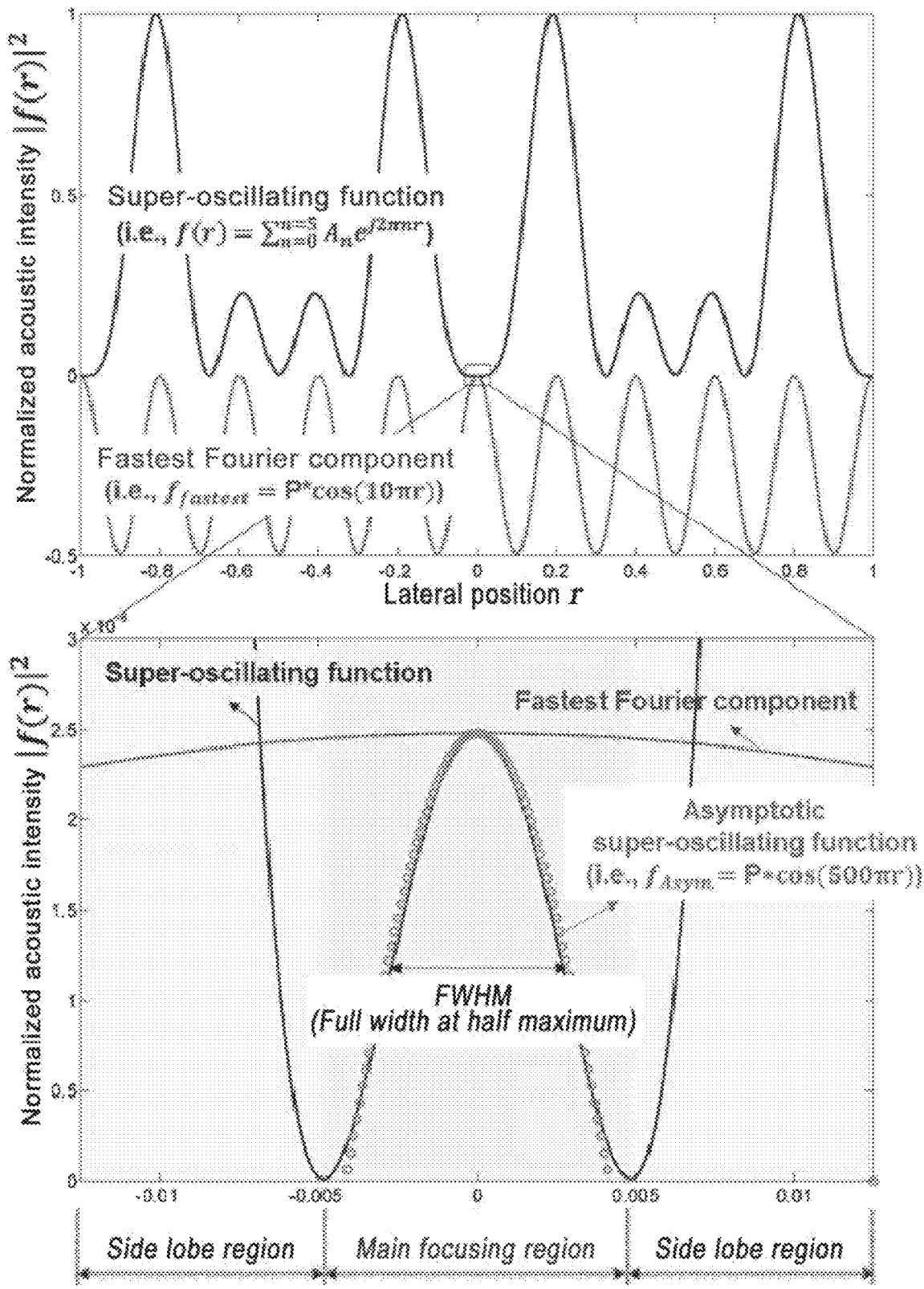
[FIG. 2]

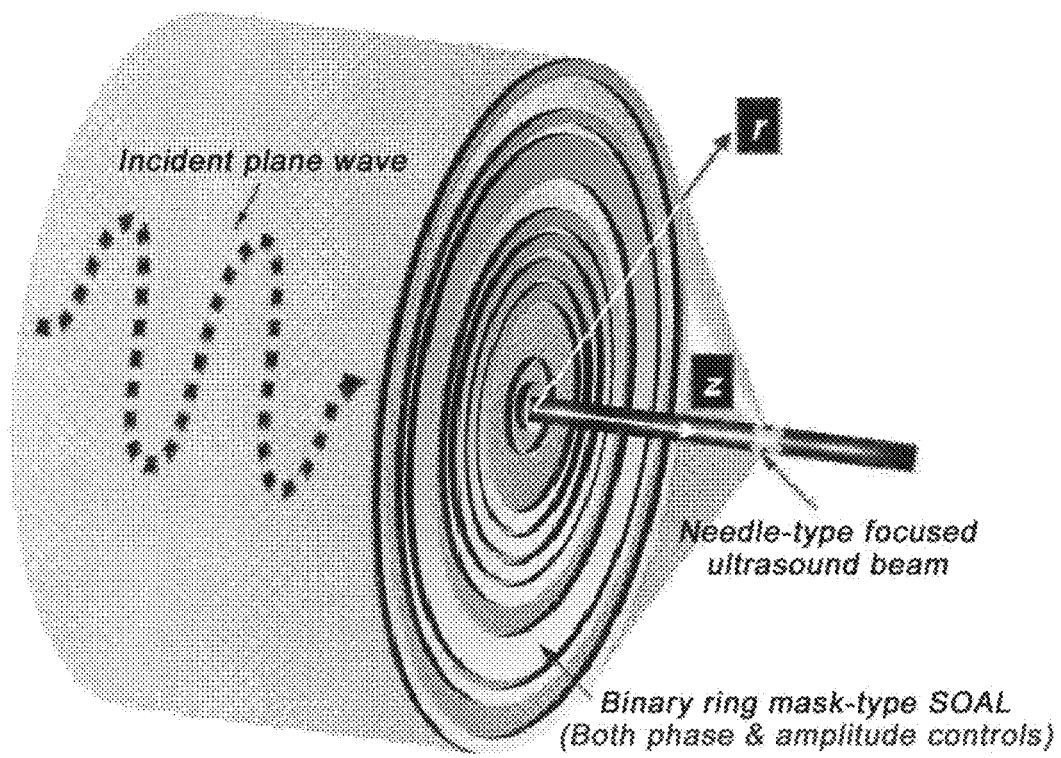
[FIG. 3]

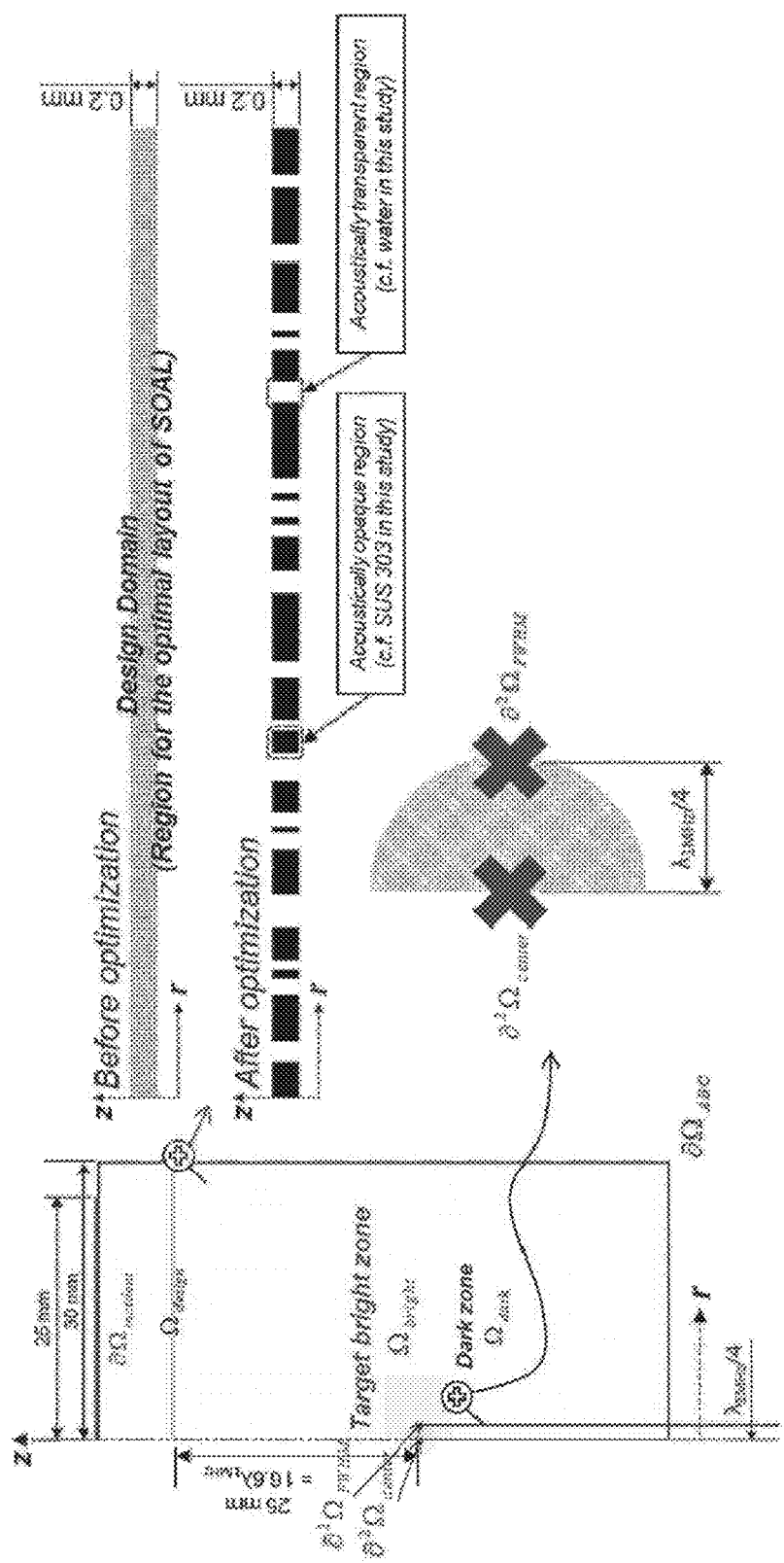
[FIG. 4]

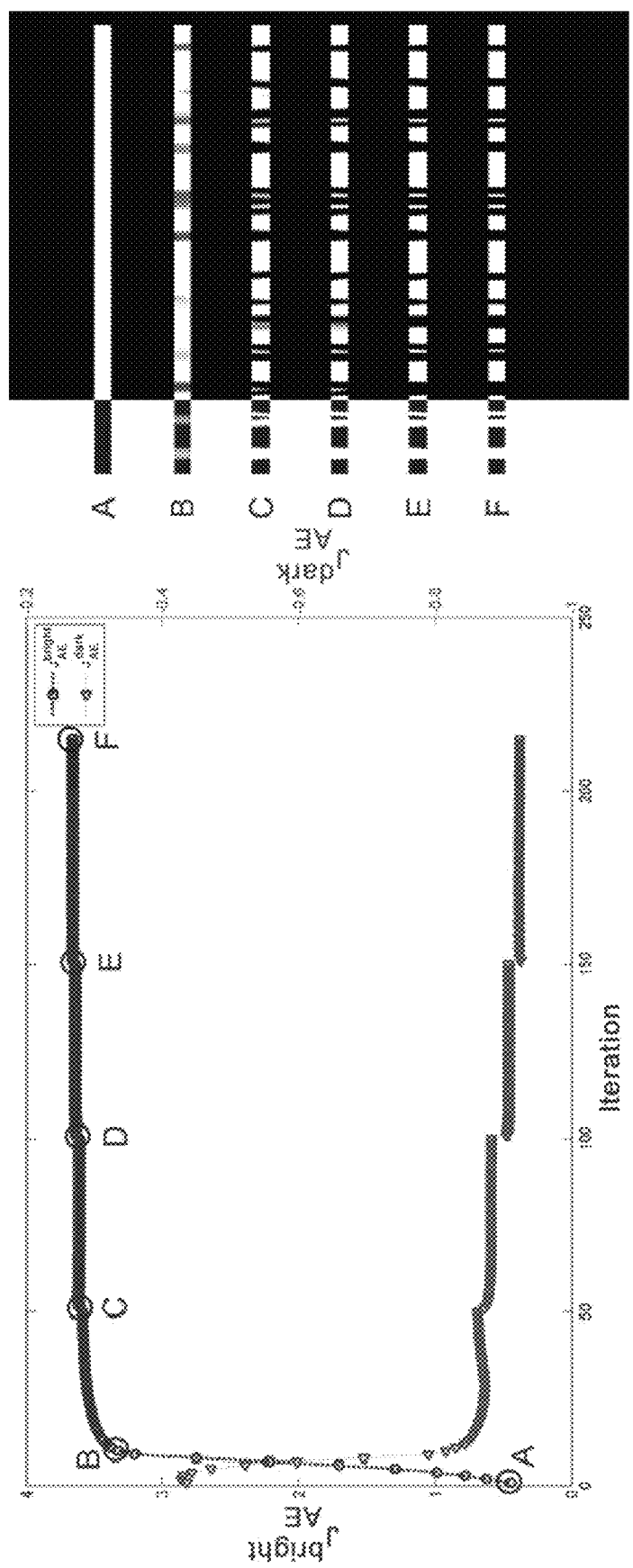
[FIG. 5]

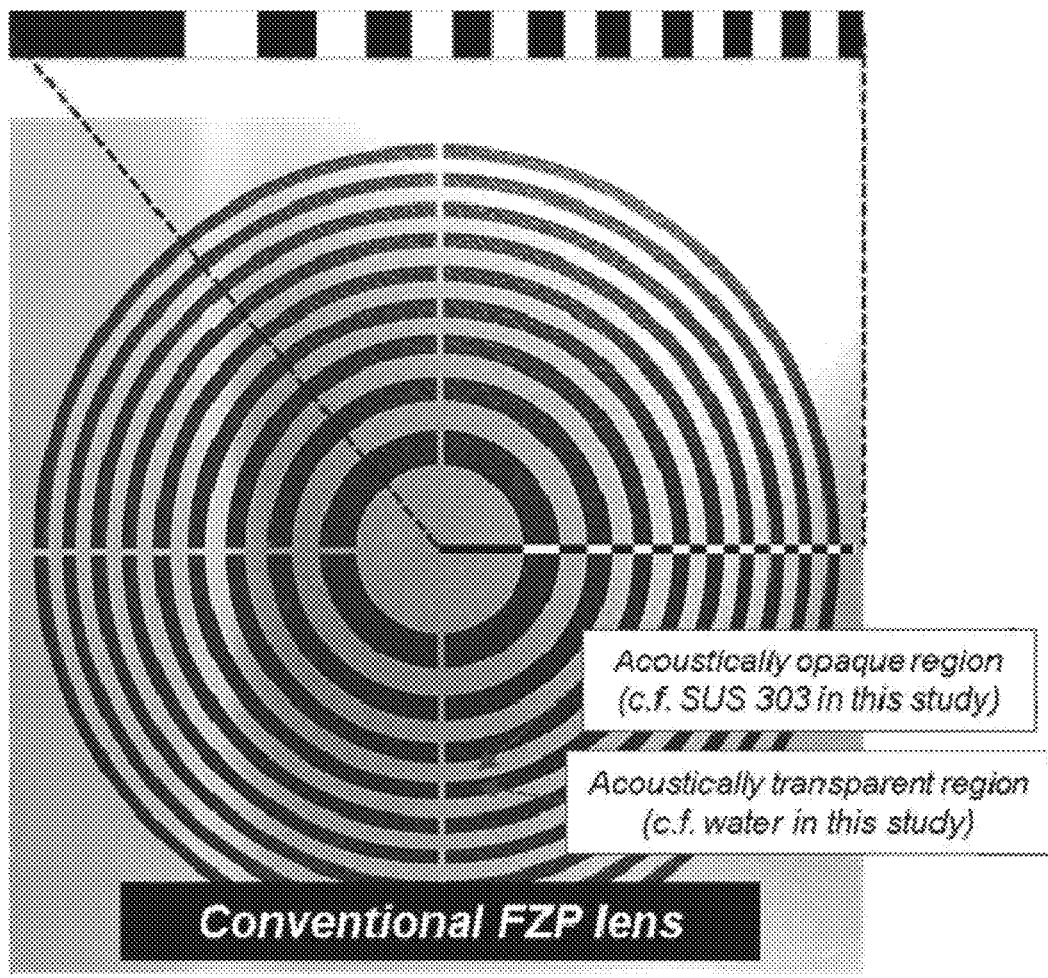
[FIG. 6]

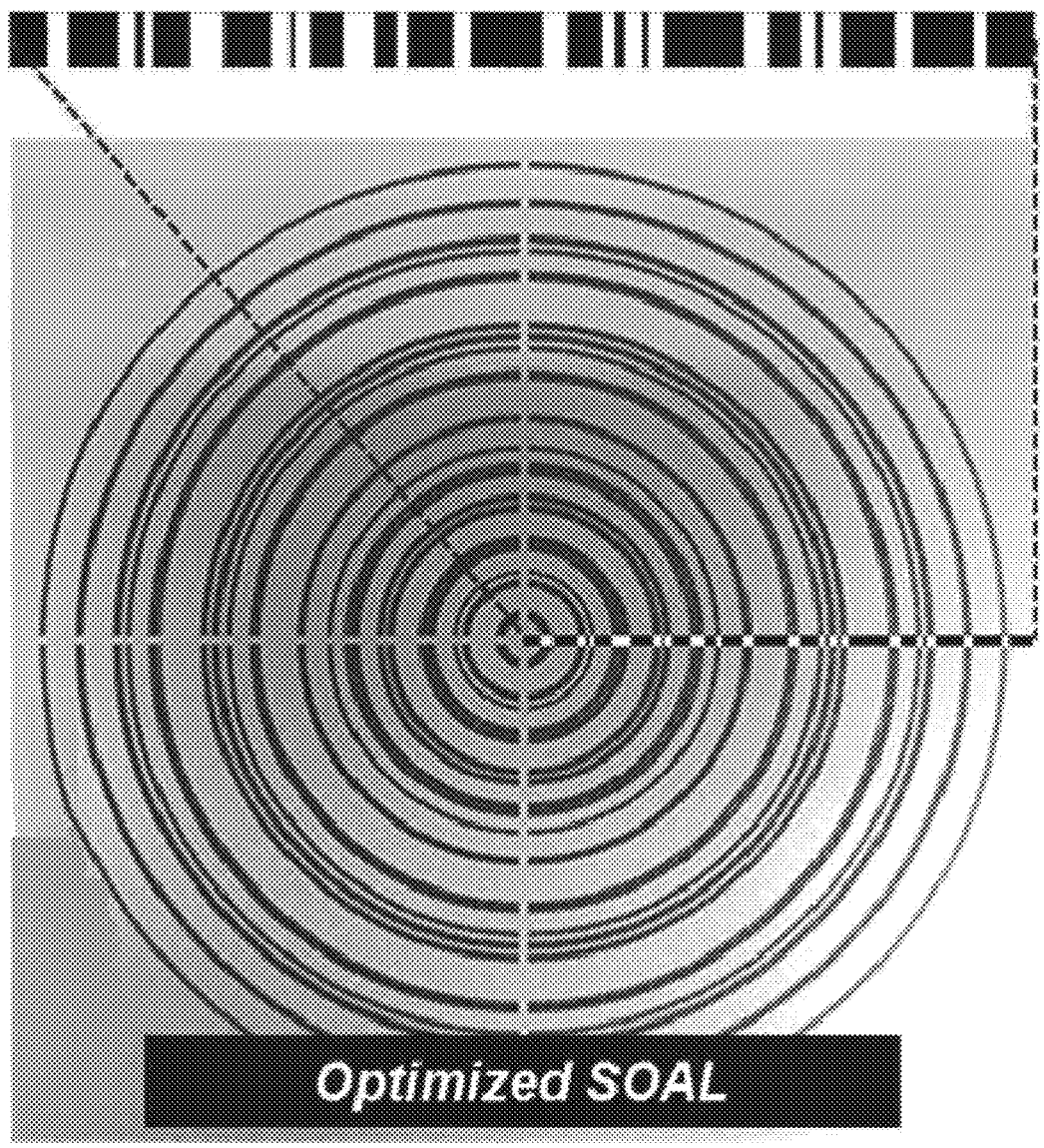
[FIG. 7]

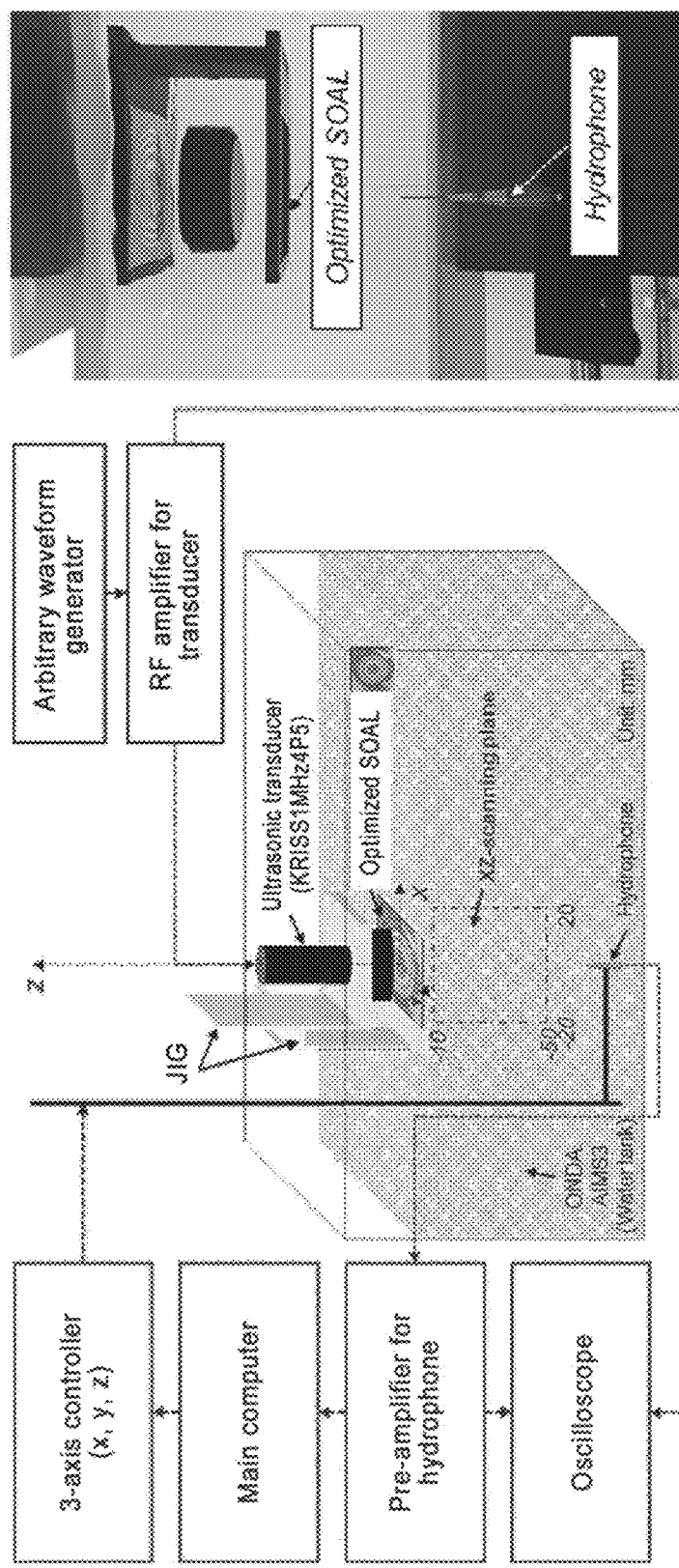
[FIG. 8]

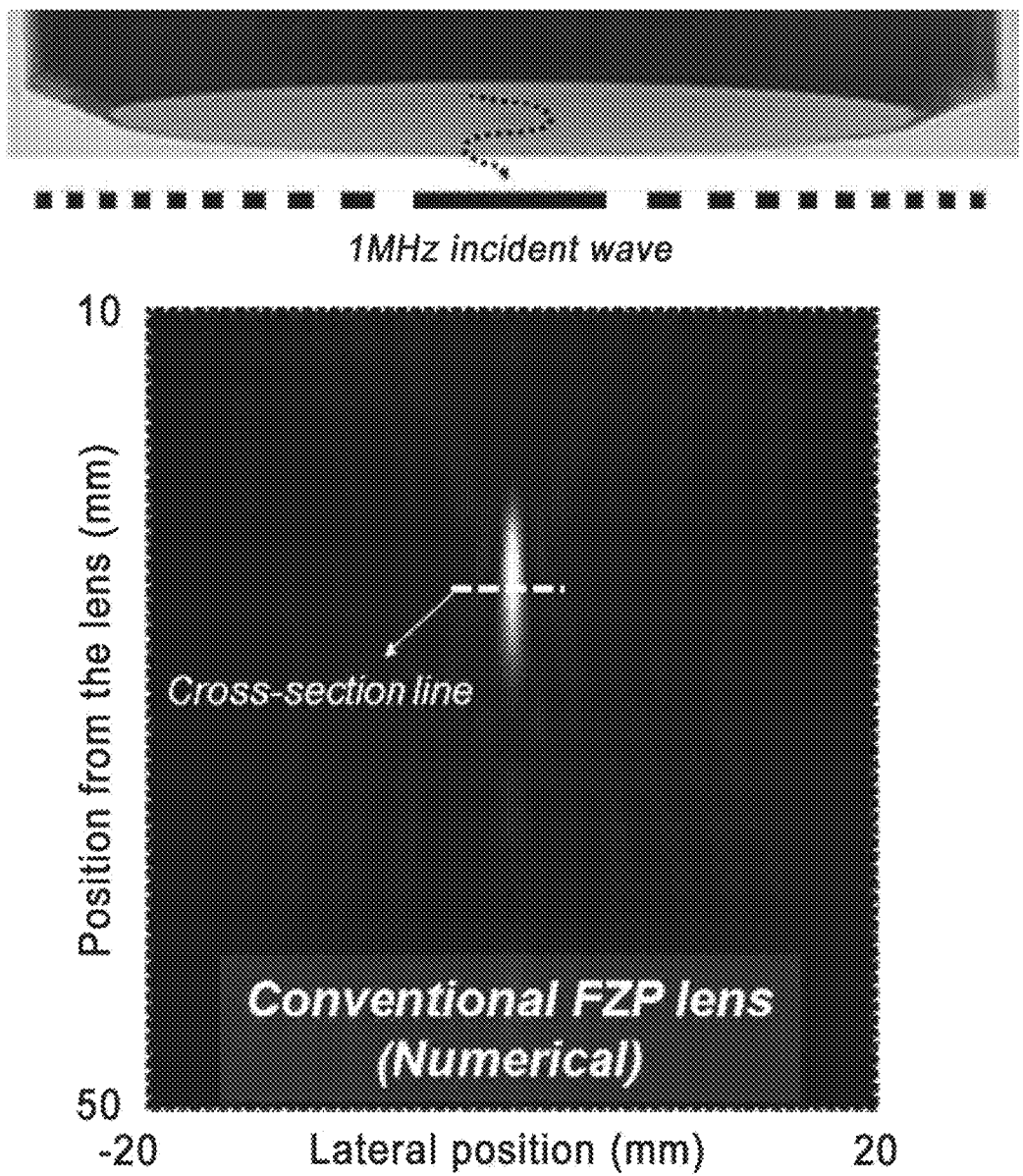
[FIG. 9]

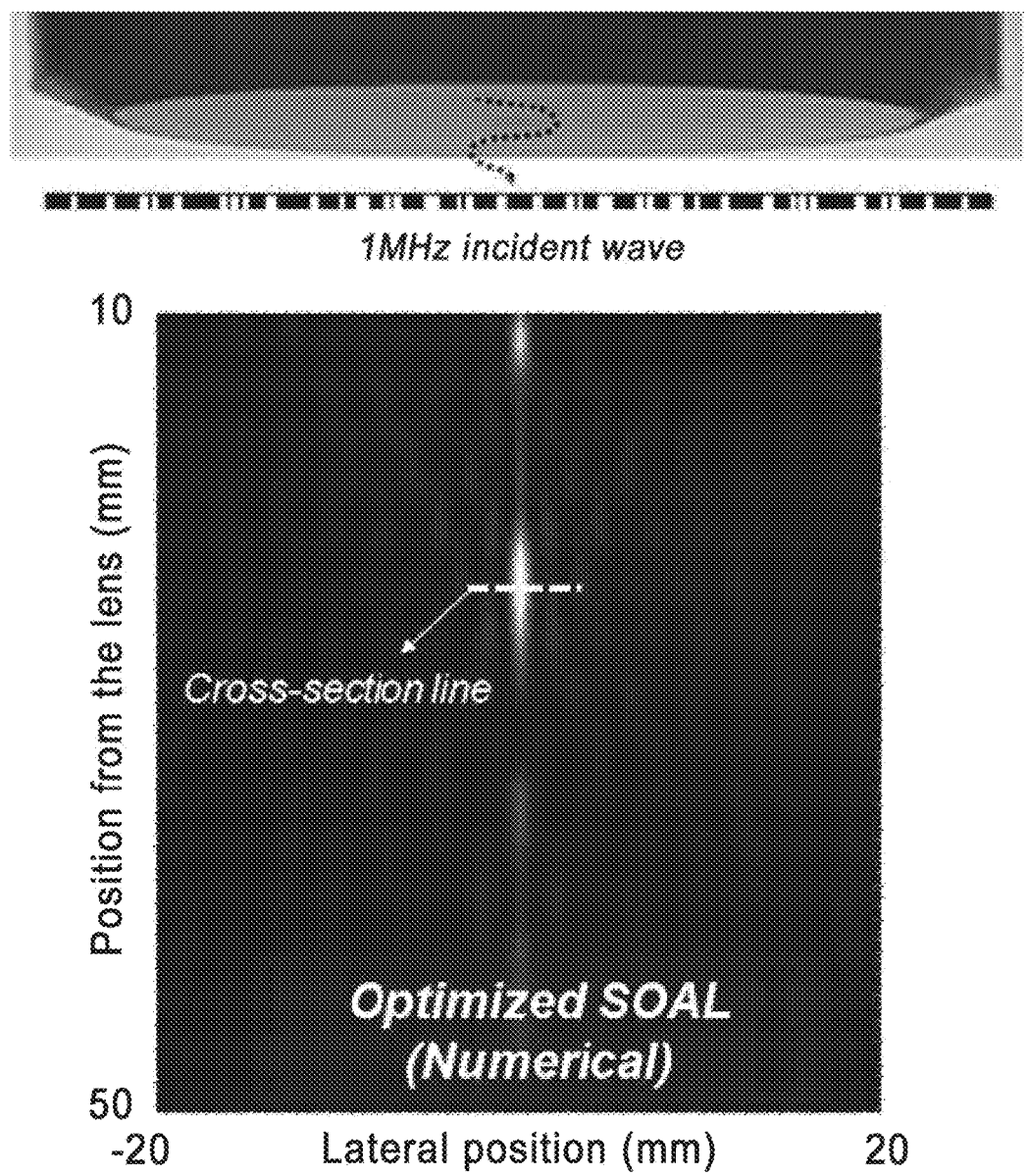
[FIG. 10]

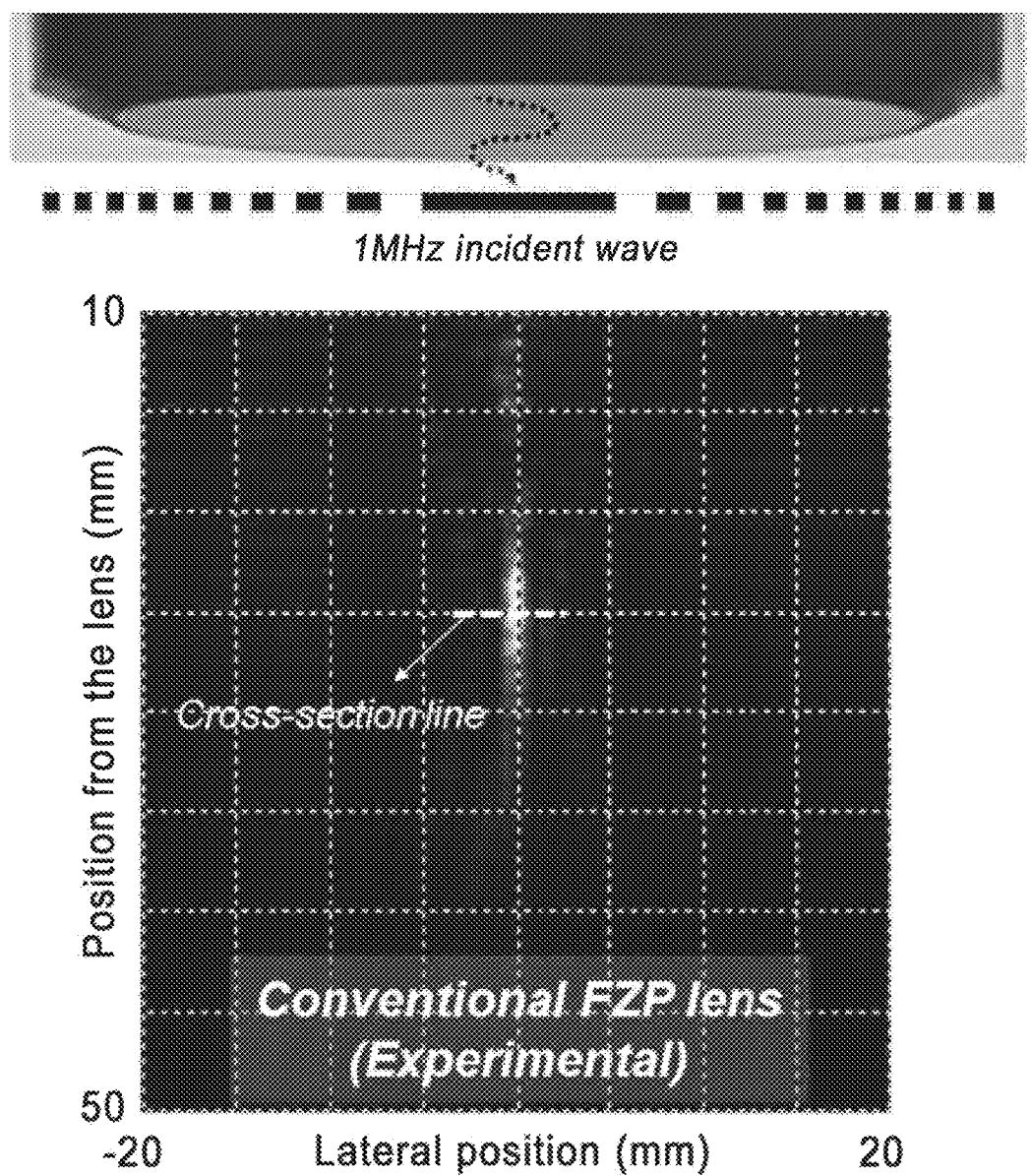
[FIG. 11]

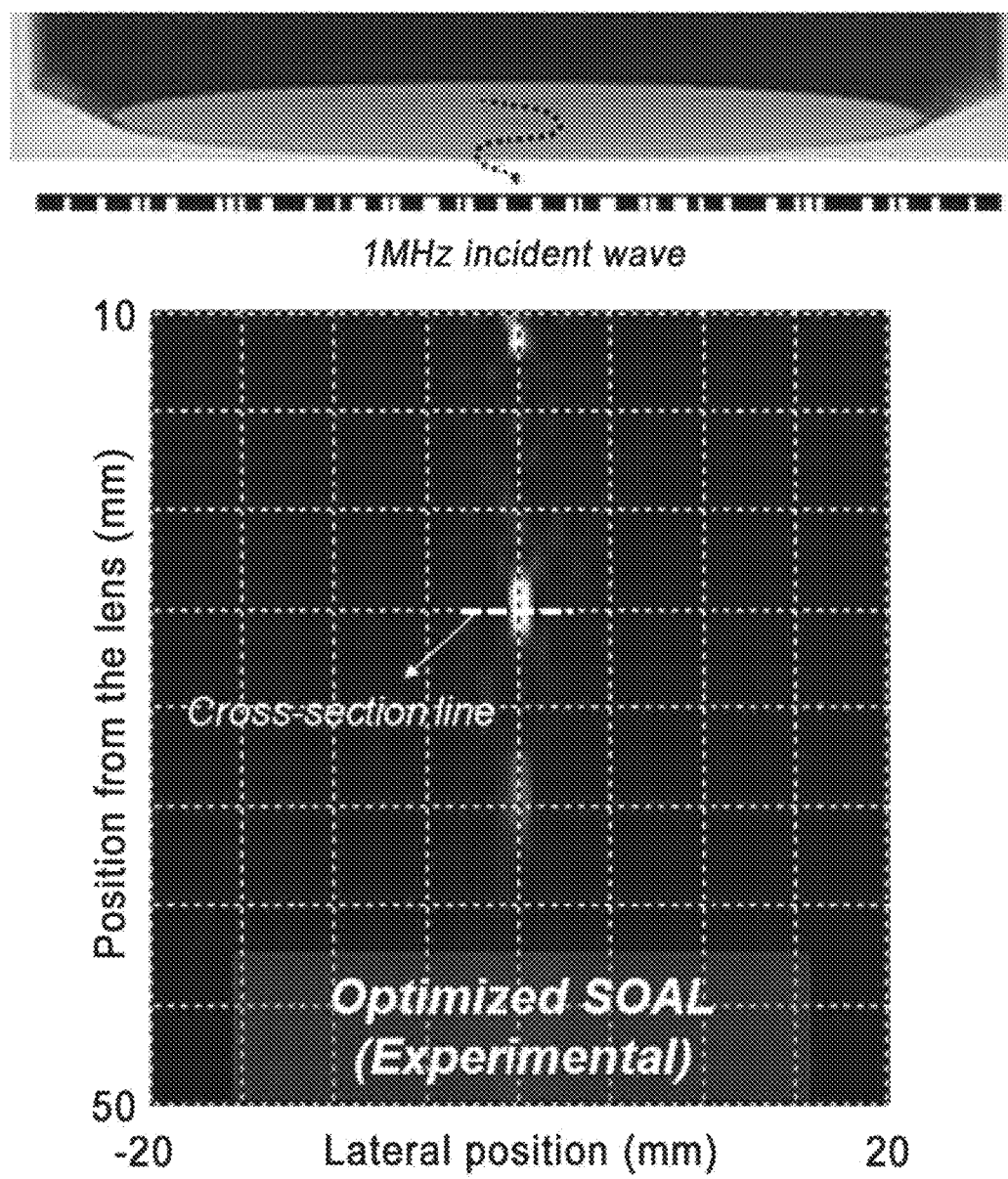
[FIG. 12]

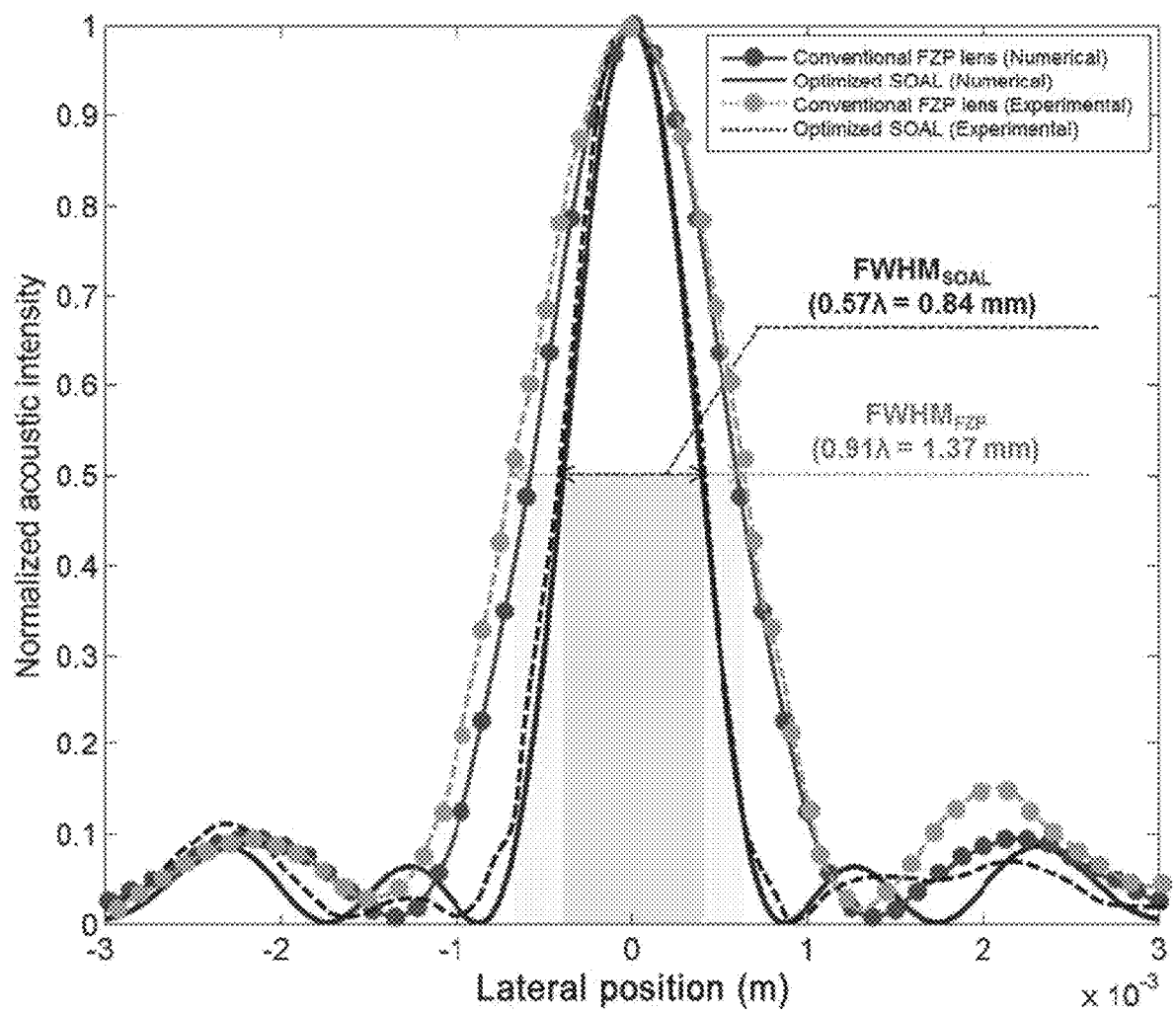
[FIG. 13]

ULTRA-THIN ACOUSTIC LENS FOR SUBWAVELENGTH FOCUSING IN MEGASONIC RANGE, AND DESIGN METHOD THEREFOR

CROSS-REFERENCE TO RELATED APPLICATIONS

This application is a national phase of PCT/KR2018/006128, filed May 30, 2018, the entire contents of which is hereby incorporated by reference.

BACKGROUND

Technical Field

The present invention is related to an ultra-thin acoustic lens for subwavelength focusing in a megasonic range and a design method thereof. More particularly, the present invention relates to an ultra-thin (≤0.14λ) acoustic lens for subwavelength focusing, which is capable of exceeding the Rayliegh diffraction limit (0.61λ/NA, NA is Numerical Aperture) referred to as Super-Oscillatory Acoustic Lens (SOAL) of the megasonic range (≥1 MHz).

The acoustic lens in accordance with the present invention is featured by allowing creating subwavelength focusing without any needs to be operated at the place the most adjacent to a subject to be imaged.

The optimized layout of the acoustic lens in accordance with the present invention can be obtained by using a topology design method referred to as Topology optimization. For this, an optimization equation will be redefined in the present invention. The optimized acoustic lens was fabricated using the photo etching process, and a subwavelength focusing performance thereof was experimentally proved through an acoustic intensity measurement system. According to measurement results, it was verified that the optimized acoustic lens can obtain an excellent focusing performance having a FWHM (Full Width at Half Maximum) of ~0.40λ/NA (NA=0.707).

Related Art

The feature of subwavelength focusing that allows concentrating acoustic energy on a very small region corresponds to the most important problem to be solved in the field of from medical ultrasonic diagnosis to therapy. This subwavelength focusing allows detecting and treating very tiny objects such as cancers and tumors which are hardly detected by the general medical ultrasonic imaging and system, meaning that many people can be provided with better medical services.

However, a conventional system has a focusing limit achieved only to an extent of the wavelength of a used wave. The focusing limit (d) is limited by the used wave (λ) and the numerical aperture (NA) of an imaging system, d=0.61λ/NA (i.e., the Rayleigh diffraction limit).

Meanwhile, in order to achieve an acoustic imaging and therapy system exceeding this diffraction limit and having the subwavelength focusing performance, the acoustic lens may be considered as a good solution.

FIG. 1 shows the typical classification of an acoustic lens according to the utilization of evanescent waves. As shown in FIG. 1, this acoustic lens can be classified into two types according to the utilization of the evanescent waves. The reason why these are related to the evanescent waves is that the evanescent waves include the micro information below the subwavelength for an object.

Firstly, as describing more particularly, the acoustic lens using the evanescent waves can be realized through a periodical (or non-periodical) micro structure that is artificially designed, Acoustic MetaMaterial (AMM). For example, provided are an acoustic super lens, an acoustic hyper lens, etc.

An AMM based lens can achieve an improved focusing limit (0.05λ/NA). However, an object to be imaged has to be adjacent to the lens so as to combine the evanescent waves of an adjacent region to the lens. Further, the mechanism of the AMM based lens was already experimentally proved, but there are still problems in controlling product qualities and energy losses when fabricating the micro structure in the megasonic range (≥1 MHz).

Therefore, if it is possible to embody the acoustic lens having a subwavelength focusing function without using any evanescent waves, this may become a very strong solution for the clinical application in effect. On the basis of this necessity, a refractive concave lens has been mainly used which is a shape being attached to the front of a source transducer. However, an application range thereof is generally limited to the large scale and the poor separation feature. It is also difficult to overcome the aforementioned diffraction limit through this type of the acoustic lens.

Therefore, in order to achieve a more minimized acoustic lens, it has been demanded to develop a planar lens which is capable of concentrating acoustic energy as modulating the phase delay of acoustic waves, such as a Fresnel Zone Plate (FZP) lens. Until now, various attempts have been made to practicalize the plate acoustic lens, but it is still a difficult problem to achieve focused wavelength through this planar lens.

In order to solve such a limit, several Acoustic MetaSurface (AMS) based lenses were proposed recently. However, the AMS based lenses have a very complicated configuration (for example, a coil ring structure or a labyrinthine structure), thus being experimentally realized only for air media in the audible frequency range.

Since it is difficult to fabricate aqueous media in the megasonic range, there is not an acoustic lens capable of being realized in fact. That is, until now, a planar ultra-thin acoustic lens having the subwavelength focusing function has not been yet realized.

Particularly, another reason why paying attention to the megasonic range (≥1 MHz) as a target operating frequency is to measure megasonic beams easily through an aqueous hydrophone having a very small diameter because the wavelength is relatively large in aqueous media. When measuring the megasonic beams through the aqueous hydrophone with apertures having a size equal to the wavelength, it is not allowable to measure a FWHM accurately due to the size effect.

Meanwhile, according to one study carried out in 2012 in the optical field, it was revealed that a superior planar optical lens called as Super Oscillatory Lens (SOL) was capable of realizing subwavelength focusing. The concept of Super Oscillation is relevant to the phenomenon that an image waveform oscillates much faster than the highest harmonic frequency component of the original image waveform in a main focusing region. This study embodied the subwavelength focusing function at the position being 10λ far from an optical lens designed by PSU (Particle Swarm Optimization) algorithm. This reported for the first time that the concept of the SOL is applicable to optical imaging as a practical solution for the subwavelength focusing. An attractive feature of the SOL is able to provide the subwavelength focusing without using evanescent waves. In other words, the subwavelength focusing feature can be achieved only through propagation. Therefore, the SOL does not need to place the object very closely, differently from conventional metamaterial based lenses.

This means that it is possible to realize far-field subwavelength focusing through the SOL. The most recently, as an alternative for the SOL in the acoustic field, was studied whether or not to realize the acoustic Super-Oscillatory phenomenon in 2014. This study theoretically achieved the subwavelength focusing by adjusting a radius of a piezoelectric ring, while failing the achievement thereof experimentally. Further, the ideal assumption that there was not mechanical crosstalk between neighboring circular ring-type piezoelectric elements was taken into account. Thus, in order to design a realizable and applicable Super-Oscillatory Acoustic Lens (SOAL), practical design elements should be taken into account, including source conditions, operating frequencies, desired subwavelength focusing regions and the thickness of a lens.

Additionally, the aforementioned studies took these design elements into account by using the design methodology based on heuristic algorithm such as PSO or GA (Genetic Algorithm). This design methodology is easily embodied but including drawbacks, i.e., incurring high costs for the calculation, taking a long time and limiting the configuration of a designed SOAL.

Therefore, in the present invention, developed was a topology reverse design process of the SOAL on the basis of topology optimization which was capable of determining optimal material distribution in the desired design domain, thereby supplementing drawbacks of the conventional design methodology and carrying out the same effectively. According to the present invention, the optimized SOAL was realized experimentally for the first time, and the subwavelength focusing function was achieved in the megasonic range (1 MHz).

SUMMARY

Technical Problem

Therefore, the present invention is provided to solve conventional problems as described above. An embodiment of the present invention aims to provide an ultra-thin acoustic lens which allows subwavelength focusing in a megasonic range.

Further, the embodiment of the present invention aims to provide a Super-Oscillatory Acoustic Lens (SOAL) for subwavelength focusing in megasonic range (≥1 MHz), which allows exceeding the Rayliegh diffraction limit (0.61λ/NA, NA is Numerical Aperture).

Further, the embodiment of the present invention aims to provide an ultra-thin acoustic lens for subwavelength focusing in the megasonic range, which allows creating subwavelength focusing without operation at the place the most adjacent to an object to be imaged, obtains the optimized layout of the acoustic lens by using a topology reverse design methodology referred to as topology optimization and has an excellent subwavelength focusing function.

Meanwhile, technical objects to be achieved in the present invention are not limited to the aforementioned technical objects, and other technical objects, which are not mentioned above, will be apparently understood to a person having ordinary skill in the art from the following description.

Technical Solution

According to a first aspect of the present invention, a super-oscillatory planar ultra-thin acoustic lens for subwavelength focusing in a megasonic range may include a plurality of concentric regions arranged in a concentric shape with reference to a center point, wherein the concentric regions are formed by crossing acoustic insulation regions for insulating incident acoustic waves and transmission regions for transmitting acoustic waves, in a radial direction from the center point, and focus the incident acoustic wave energy onto a subwavelength region, the acoustic lens is composed of opposite surfaces having a flat surface, and has a plate shape having a constant thickness, and a layout which is a radius of each of the plurality of acoustic insulation regions and transmission regions in the concentric region, is determined by a topology optimization reverse design method and provided being spaced apart from a transducer.

According to another aspect of the present invention, the acoustic lens may be composed of a binary ring mask-type super-oscillatory acoustic lens.

According to another aspect of the present invention, during topology optimization process, acoustic energy in a main focusing region may be gradually increased, allowing optimization.

According to another aspect of the present invention, the acoustic lens may be provided being not attached to a transducer but spaced apart therefrom, allowing being replaced with other acoustic lenses having different, various layouts.

According to another aspect of the present invention, an FWHM (Full Width at Half Maximum) in the main focusing region may be a Rayleigh diffraction limit or under.

According to another aspect of the present invention, the FWHM (Full Width at Half Maximum) in the main focusing region is 0.5λ/NA or under.

According to another aspect of the present invention, a thickness of the acoustic lens may be 0.5λ or under.

According to another aspect of the present invention, a layout design of the acoustic insulation region and the transmission region may be determined by following formula 2:

$$\max_{\gamma_e} J_0 = \text{Acoustic Energy}|_{bright} = \quad [\text{Formula 2}]$$

$$J_{AE}^{bright} = \frac{1}{2 p_{water} c_{water}} \int_{\Omega_{bright}} |p|^2 d\Omega$$

$$\text{subject to } g_1 = \frac{\int_{\Omega_{design}} \gamma_e d\Omega}{(VFF) V_{design}} - 1 \leq 0$$

$$g_2 = \left( \frac{|p|^2_{\partial^2 \Omega FWHM}}{0.5 |p|^2_{\partial^2 \Omega design}} - 1 \right)^2 \leq \varepsilon$$

$$\gamma_e = [\gamma_1, \gamma_2, \ldots, \gamma_{NE}] \in (0 \sim 1)$$

in the formula 2, p is an acoustic pressure, $\gamma_e$ is a design variable which is varied in an interval of 0 to 1 during phase optimization, VFF is an essential volume ratio which defines a ratio of an opaque region to an entire design domain, $V_{design}$ is a volume of the entire design domain, e is a threshold for relaxation of a constraint ($g_2$), and NE is a sum of design variables.

According to another aspect of the present invention, according to updated design variables ($\gamma_e$), material distribution in the design domain may be determined on the basis of following formula 3a and formula 3b:

$$p(\gamma_e) = \left(\frac{1}{\rho_{water}} + \gamma_e^{q1}\left(\frac{1}{\rho_{SUS303}} - \frac{1}{\rho_{water}}\right)\right)^{-1} \quad \text{[Formula 3a]}$$

$$c(\gamma_e) = \left(\frac{1}{c_{water}} + \gamma_e^{q1}\left(\frac{1}{c_{SUS303}} - \frac{1}{c_{water}}\right)\right)^{-1} \quad \text{[Formula 3b]}$$

in the formulae 3a and 3b, $q^1$ and $q^2$ are penalty coefficients for a mass density ($\rho$) and an acoustic speed (c), respectively.

According to a second aspect of the present invention, a design method of a super-oscillatory planar ultra-thin acoustic lens for subwavelength focusing in a megasonic range may include steps of: determining a design domain for an optimal layout; setting up a desired main focusing region and determining a transmission material and an acoustic insulation material; setting up a desired FWHM and adopting a constraint; optimizing a layout of the transmission region and the acoustic insulation region by a topology optimization reverse design method; and fabricating an acoustic lens through a photo etching method on the basis of the optimized layout.

According to another aspect of the present invention, during topology optimization process, acoustic energy may be gradually increased in a main focusing region, allowing optimization.

According to another aspect of the present invention, a layout design of the acoustic insulation region and the transmission region may be determined by following formula 2:

$$\max_{re} J_0 = \text{Acoustic Energy}]_{bright} = \quad \text{[Formula 2]}$$

$$J_{AE}^{bright} = \frac{1}{2 p_{water} c_{water}} \int_{\Omega_{bright}} |p|^2 d\Omega$$

$$\text{subject to } g_1 = \frac{\int_{\Omega_{design}} \gamma_e d\Omega}{(VFF)V_{design}} - 1 \leq 0$$

$$g_2 = \left(\frac{|p|^2_{\Omega FWHM}}{0.5|p|^2_{\Omega design}} - 1\right)^2 \leq \varepsilon$$

$$\gamma_e = [\gamma_1, \gamma_2, \ldots, \gamma_{NE}] \in (0\sim1)$$

in the formula 2, p is an acoustic pressure, $\gamma_e$ is a design variable which is varied in an interval of 0 to 1 during phase optimization, VFF is an essential volume ratio which defines a ratio of an opaque region to an entire design domain, $V_{design}$ is a volume of the entire design domain, e is a threshold for relaxation of a constraint ($g_2$), and NE is a sum of design variables.

According to another aspect of the present invention, according to updated design variables ($\gamma_e$), material distribution in the design domain may be determined on the basis of following formula 3a and formula 3b:

$$p(\gamma_e) = \left(\frac{1}{\rho_{water}} + \gamma_e^{q1}\left(\frac{1}{\rho_{SUS303}} - \frac{1}{\rho_{water}}\right)\right)^{-1} \quad \text{[Formula 3a]}$$

$$c(\gamma_e) = \left(\frac{1}{c_{water}} + \gamma_e^{q1}\left(\frac{1}{c_{SUS303}} - \frac{1}{c_{water}}\right)\right)^{-1} \quad \text{[Formula 3b]}$$

in the formulae 3a and 3b, $q^1$ and $q^2$ are penalty coefficients for a mass density ($\rho$) and an acoustic speed (c), respectively.

According to another aspect of the present invention, during optimizing process, the design variables may be updated on the basis of slope information calculated by AVM (Adjoint Variable Method).

According to another aspect of the present invention, during optimizing process, during the optimizing process, a heaviside projection filtering method having beta-continuation may be repeated.

Advantageous Effects

An acoustic lens according to an embodiment of the present invention is capable of providing an ultra-thin acoustic lens which allows subwavelength focusing in the megasonic range.

Further, an ultra-thin acoustic lens for subwavelength focusing in the megasonic range according to the embodiment of the present invention has an effect capable of exceeding Rayliegh diffraction limit (0.61λ/NA, NA is Numerical Aperture).

In addition, the ultra-thin acoustic lens for subwavelength focusing in the megasonic range according to the embodiment of the present invention has effects capable of allowing the generation of subwavelength focusing without operation at the place the most adjacent to a subject to be imaged and of obtaining the optimal layout of the acoustic lens by using a topology reverse design methodology referred to as topology optimization.

Meanwhile, advantageous effects to be obtained in the present invention are not limited to the aforementioned effects, and other effects, which are not mentioned above, will be apparently understood to a person having ordinary skill in the art from the following description.

BRIEF DESCRIPTION OF THE DRAWINGS

The accompanying drawings of this specification exemplify a preferred embodiment of the present disclosure, the spirit of the present disclosure will be more clearly understood from the following detailed description taken in conjunction with the accompanying drawings, and thus it will be understood that the present disclosure is not limited to only contents illustrated in the accompanying drawings.

FIG. 1 shows traditional classification of acoustic lenses according to the usage of evanescent waves.

FIG. 2 and FIG. 3 show a megasonic SOAL according to the present invention and basic mechanism thereof.

FIG. 4 and FIG. 5 show a numerical model for both design and analysis of a binary ring mask-type SOAL.

FIG. 6 is a top view showing a layout of a fabricated FZP lens.

FIG. 7 is a top view of optimized SOL fabricated according to an embodiment of the present invention.

FIG. 8 shows a set-up of an experiment for measuring an acoustic filed through a conventional FZP lens and the optimized SOAL.

FIG. 9 is an acoustic intensity field numerically calculated through the conventional FZP lens.

FIG. 10 is an acoustic intensity field numerically calculated through the optimized SOAL according to the present invention.

FIG. 11 is an acoustic intensity field experimentally calculated through the conventional FZP lens.

FIG. 12 is an acoustic intensity field experimentally calculated through the optimized SOAL according to the present invention.

FIG. 13 shows a comparative graph of a normalized acoustic intensity filed.

DETAILED DESCRIPTION

Best Mode

Hereinafter, described are the proof of a super-oscillatory phenomenon and the application thereof to a subwavelength focusing acoustic lens. The super-oscillatory mechanism of a megasonic super-oscillatory acoustic lens provided in the present invention can be proved simply in a one dimensional (1D) wave composed of six domains of Fourier components according to an approaching method. A 1D waveform can be defined as f(r) in Formula 1.

$$f(\gamma) = \sum_{n=0}^{n-5} A_n e^{j2\pi n r} \quad \text{[Formula 1]}$$

in the formula 1, r is a radius of a source transducer, meaning a normalized position along with the lateral direction. Herein, An uses a Fourier coefficient (wherein, $A_0$=19.0123, $A_1$=−2.7348, $A_2$=−15.7629, $A_3$=−17.9047, $A_4$=−1.0000, $A_5$=18.4910).

FIG. 2 and FIG. 3 show a megasonic SOAL according to the present invention and basic mechanism thereof. FIG. 2 is the basic mechanism of 1D super-oscillatory functions, wherein the upper panel represents a super-oscillatory function (blue color) and the fastest Fourier component (red color), and the lower panel represents the expansion over a function showing a narrow peak around r=0. The super-oscillatory function can be divided into two, i.e., a desired main focusing region and an undesired side lobe. As shown in FIG. 3, the SOAL having a binary ring mask controls both phase and amplitude, allowing transforming an incident acoustic plane wave into a needle-type focused beam.

That is, in FIG. 2, shown are an acoustic intensity of the original wave |f(r)|² (i.e., blue colored solid line) and the fastest Fourier component ($f_{fastest}$=P*cos(10πr)) (i.e., red colored broken line).

Herein, the wording "the fastest" means an oscillatory component being the fastest spatially by the highest frequency component of the original waveform. As shown in the lower panel in FIG. 2, there is a narrow peak, $f_{Asym}$=P*cos(500πr)) being approximately 10 times narrower than the fastest Fourier component of the original wave around r=0.

In this 1D, super-oscillation means a waveform which oscillates faster than the highest harmonic frequency component of the original wave in a limited interval (i.e., desired main focusing region). Therefore, a subwavelength focusing feature is guaranteed only in this finite region. As shown in this D1, super-oscillatory phenomenon-based subwavelength focusing can be accomplished as controlling an amplitude (Fourier coefficient) and a phase (2πnr) of the waveform diffracted from a micro-slit of the lens.

Meanwhile, the subwavelength feature of the super-oscillatory wave should involve a high amplitude region outside the desired main focusing region. An undesired region is referred to as a side lobe. In order to improve the focusing performance (i.e., narrower FWHM) of the lens, the undesirable side lobe is an unavoidable result, since the relationship between the desired region and the undesired region has a trade-off performance. Therefore, it is needed to select an appropriate scale of the desired main focusing region in order to practically design the SOAL.

As shown in FIG. 3, the SOAL can be achieved through the binary ring mask having spatially changed phase and amplitude. A binary ring mask-type SOAL allows embodying super-oscillatory phenomenon-based subwavelength focusing, which can be fabricated by using the conventional micro-processing technology such as an etching process. Due to this advantage, the binary ring mask-type SOAL was applied to the present invention as a method for achieving subwavelength focusing. The original waveform can be transformed into a super-oscillatory waveform having a subwavelength focusing feature by using this SOAL.

Moving on to the next, in order to design an optimal layout of the binary ring mask-type SOAL, described is an optimization formula capable of quantification physically.

Since a design optimizing process according to the present invention allows phase changes such as increases or decreases in the number of holes, applied was topology optimization as one of the most flexible type of reverse design methods.

In order to obtain the optimal layout of the binary ring mask-type SOAL, a numerical model should be taken into account for both analysis and design. FIG. 4 and FIG. 5 show the numerical model for both design and analysis of the binary ring mask-type SOAL, and FIG. 4 shows the configuration of the numerical model for designing topology of a layout of the binary ring mask-type SOAL. Herein, in order to solve problems in acoustic wave propagation effectively in a megasonic range on the basis of Helmholtz equation, used was a two dimensional (2D) line symmetry finite element model. FIG. 5 shows topology optimization history, and an image shows evolution of a 2D topology layout of acoustic energy and SOAL during the optimizing process. A black colored region represents SUS 303 material and a white colored region represents water. The acoustic energy ($J_{AE}^{bright}$) is gradually increased in the main focusing region (i.e., red-semicircular target bright zone in FIG. 4)

In FIG. 4, in order to solve problems in acoustic wave propagation effectively in the megasonic range on the basis of Helmholtz equation, used was the two dimensional (2D) line symmetry finite element model. A region for the optimal layout of the SOAL (i.e., design domain, $\Omega_{design}$) is positioned being 10 mm far from the source transducer capable of being modeled by radiation boundary conditions. In order to avoid wave reflection, the analysis and design domains are grouped in an absorbing boundary.

The radius and height of the design domain (i.e., thickness of SOAL) are 30 mm and 0.2 mm, respectively. Then, the desired main focusing region (i.e., red-semicircular target bright zone in FIG. 4) is positioned being 25 mm (i.e., approximately 16.6λ) far from the design domain. Meanwhile, acoustically opaque and transparent regions are required for designing the layout of the SOAL. For this, in an embodiment of the present invention, each SUS 303 material (mass density, $\rho_{SUS\ 303}$=8,000 kg/m³ and acoustic speed, $c_{SUS}$ 303=4,484 m/s) and water (mass density, $\rho_{water}$=1,000 kg/m³ and acoustic speed, $c_{water}$ 303=1,482 m/s) is used in each of the acoustically opaque and transparent regions.

Meanwhile, in order to topologically design the binary ring mask-type SOAL for subwavelength focusing, it is needed to take the side lobe into account besides the main focusing region, with maintaining a band-limited feature of the main focusing region (i.e., red-semicircular target bright zone in FIG. 4). For setting up the topology optimization, a constraint related to a desired FWHM is adopted. In general, acoustic lenses are optimized by maximizing only acoustic energy ($J_{AE}^{bright}$) in the main focusing region. However, in order to guarantee the subwavelength focusing feature of the SOAL, adopted was a constraint (g2) related to the desired FWHM newly besides a target function ($J_{AE}^{bright}$). This is very simple in an aspect of design but corresponds to a very strong optimization formula. Therefore, in the present invention, the topology optimization set-up for designing the layout of the SOAL can be defined by the following formula 2.

$$\max_{re} J_0 = \text{Acoustic Energy}]_{bright} = \quad [\text{Formula 2}]$$

$$J_{AE}^{bright} = \frac{1}{2\rho_{water} c_{water}} \int_{\Omega_{bright}} |p|^2 d\Omega$$

$$\text{subject to } g_1 = \frac{\int_{\Omega_{design}} \gamma_e d\Omega}{(VFF)V_{design}} - 1 \le 0$$

$$g_2 = \left(\frac{|p|^2_{\partial^2 \Omega FWHM}}{0.5|p|^2_{\partial^2 \Omega design}} - 1\right)^2 \le \varepsilon$$

$$\gamma_e = [\gamma_1, \gamma_2, \ldots, \gamma_{NE}] \in (0 \sim 1)$$

wherein, p is an acoustic pressure, and $\gamma_e$ is a design variable which is varied in an interval of 0 to 1 during phase optimization. VFF is an essential volume ratio which defines a ratio of an opaque region to an entire design domain. $V_{design}$ is a volume of the entire design domain. e is a threshold for relaxation of a constraint ($g_2$). In the embodiment of the present invention, $10^{-3}$ is selected as this value. NE is the sum of design variables. Herein, according to updated design variables ($\gamma_e$), material distribution in the design domain can be determined on the basis of following formula 3a and formula 3b. When $\gamma_e$=0, an acoustic material corresponds to water (i.e., acoustically transparent region), while corresponding to SUS303 (i.e., acoustic insulation region) when $\gamma_e$=1.

$$p(\gamma_e) = \left(\frac{1}{\rho_{water}} + \gamma_e^{q_1}\left(\frac{1}{\rho_{SUS303}} - \frac{1}{\rho_{water}}\right)\right)^{-1} \quad [\text{Formula 3a}]$$

$$c(\gamma_e) = \left(\frac{1}{c_{water}} + \gamma_e^{q_1}\left(\frac{1}{c_{SUS303}} - \frac{1}{c_{water}}\right)\right)^{-1} \quad [\text{Formula 3b}]$$

wherein, $q^1$ AND $q^2$ are penalty coefficients for a mass density ($\rho$) and an acoustic speed (c), respectively. These penalty coefficients are used for increasing a convergence speed of the optimizing process. 1.5 is selected as these values in the embodiment of the present invention. MMA (Moving Asysmptotes) method is used as the following optimizing algorithm.

This type of optimizing algorithm requires the first-order differentiation (i.e., gradient) information of a target function called a design sensitivity threshold in order to update the design variables. Therefore, in the present invention, in order to calculate this gradient information, effective design sensitivity analysis is carried out on the basis of Adjoint Variable Method (AVM).

FIG. 5 shows the entire process for a 2D topology optimized layout of acoustic energy and SOAL. Since the optimizing process starts from a region fully filled with a solid material (i.e., SUS 303), an initial layout is represented being similar to a black colored square. Herein, in order to find out a pure 0-1 solution (i.e., a complete binary ring mask-type SOAL), a heaviside projection filtering method having beta-continuation is applied at every fiftieth time.

Accordingly, the target function (i.e., acoustic energy $J_{AE}^{bright}$) slightly jumps at every fiftieth time as shown in the topology optimization history (FIG. 5). This optimization history verifies that the SOAL layout is converged well during the optimizing process. Further, the proposed topology design methodology can be applied to the reverse design of a multilayer-type SOAL in the same way as the above besides the aforementioned monolayer SOAL.

Description of Embodiments

Hereinafter, described is an experimental result for subwavelength focusing of an optimized super-oscillatory acoustic lens (SOAL) according to an embodiment of the present invention. In order to examine a subwavelength focusing performance of the optimized SOAL, a circular form was fabricated through photo etching, then performing an experiment to measure an acoustic field radiated from the optimized SOAL using an acoustic intensity measurement system. The subwavelength focusing performance of the optimized SOAL was examined as compared to a conventional FZP lens having the same primary focal length (i.e., position of a desired main focusing region) as that of the optimized SOAL. A layout of the conventional FZP lens having the primary focal length (F) can be obtained by using the following formula 4.

$$b_n = \sqrt{n\lambda F + \left(\frac{n\lambda}{2}\right)^2} \quad [\text{Formula 4}]$$

wherein, $b_n$ is a radius of the $n_{th}$ circular region. N=1, 2, ... N, wherein N is the total number of regions. F is a main focal length, λ is a used acoustic wavelength. The conventional FZP acoustic lens and the optimized SOAL according to the present invention were fabricated by using photo etching as shown in FIGS. 6 and 7. FIG. 8 shows, as a graphic, the experiment set-up for measuring the acoustic field through the conventional FZP lens and the optimized SOAL according to the present invention. That is, FIG. 6 shows the fabricated FZP lens, and determining a layout (i.e., scale of the circular region) by formula 4. FIG. 7 shows the monolayer optimized SOAL fabricated according to the embodiment of the present invention. FIG. 8 shows the experiment set-up for measuring the acoustic field through the conventional FZP lens and the optimized SOAL.

As shown in FIG. 8, in an example of the present invention, in order to measure the acoustic filed effectively, a jig was fabricated, allowing easily controlling a separability of the SOAL (See right-hand side in FIG. 8). Tested were effects of various planar lenses on a megasonic focusing performance for only one source transducer through this jig.

An apparatus for the experiment according to the example of the present invention as shown in FIG. 8 is composed of a transducer, a hydrophone, an arbitrary waveform generator, an amplifier and a water tank. The transducer ("KRISSMHz4p5", (using international standard transducer developed by KRISS)) is used for generating a plane wave.

A needle-type hydrophone (Precision Acoustics) in which an underwater pre-amplifier was equipped and a radius of the needle is 500 μm is used in accurately measuring the acoustic filed through an acoustic lens. Further, in order to generate a fifteen cycle tone-burst signal of 1 MHz to 200 mV$_{rms}$, an arbitrary waveform generator (33250A, Agilent Technologies) was used. In order to amplify the generated tone-burst signal, an RF amplifier (2100L RF amplifier, Electronics & Innovation, Ltd.) was used. The whole equipment was installed to a deionized and degasified tank, then measuring the acoustic field passing through the acoustic lens with an acoustic intensity measurement system (AIMS III with Soniq Software, ONDA).

Prior to indicating an experimentally measured result, a numerically calculated result should be provided first. FIGS. 9 and 10 show the acoustic fields numerically calculated through the conventional FZP lens (left-hand side, a) and the optimized SOAL (right-hand side, b), respectively. Correspondingly thereto, FIGS. 11 and 12 show the acoustic fields measured experimentally. Herein, all results shown in FIG. 13 are standardized by the maximum value of the measured acoustic intensity.

In the embodiment of the present invention, a Finite Element Method (FEM) based on commercial software, COMSOL Multiphysics and MATLAB was used in then numerical analysis and design optimization of the SOAL. Materials used in the simulation were water and SUS 303. Time-harmonic analysis is used in calculating the acoustic field through the optimized SOAL. The secondary Sommerfeld absorbing boundary conditions are set up in the external boundary of a simulation region in order to remove boundary reflected acoustic waves. The source transducer approximates a plane wave boundary condition. The largest scale of a mesh element is set up being smaller than 1/10 of wavelength.

FIG. 5 shows, in an aspect of the subwavelength focusing performance, a comparison of the numerical and experimental results of the monolayer optimized SOAL. FIGS. 9 and 10 show the acoustic intensity numerically calculated by the conventional FZP lens (FIG. 9) and the optimized SOAL (FIG. 12). FIGS. 11 and 12 show the experimentally measured acoustic intensity fields radiated by the conventional FZP lens (FIG. 11) and the optimized SOAL (FIG. 12). FIG. 13 is a comparison graph of a normalized acoustic intensity field, indicating a cross-sectional measurement line in accordance with a lateral direction as a broken line.

Measurement values are made on an XZ-scanning plane (i.e., 40 mm×40 mm) of FIG. 8. As shown in FIG. 9 to FIG. 12, experimentally measured values and numerically calculated fields almost coincide with each other. Then, acoustic energy as shown in FIGS. 10 and 12, is focused on the desired main focusing region (i.e., main focal length, F=25 mm) very easily through the optimized SOAL. FIG. 13 shows a cross-sectional plot of the normalized acoustic intensity in FIG. 9 to FIG. 12, comparing lateral FWHM thoroughly.

A cross-sectional line for plotting is indicated as a broken line. As mentioned above, in order to accurately evaluate the subwavelength focusing performance of the optimized SOAL, NA should be taken into account. NA is determined by a radius of an input source transducer ($r_{source}$) and a designated basic focal length (F) and represented as NA=sin (tan$^{-1}$($r_{source}$/F)). NA for the optimized SOAL having a monolayer according to the embodiment of the present invention is approximately 0.707. Therefore, the focusing limit of the conventional acoustic lens (i.e., Rayleigh diffraction limit) is 0.61λ/NA≈0.86λ≈1.28 mm.

The numerical and experimental results in FIG. 5 and table 1 show that the optimized SOAL has two important features in an aspect of the focusing performance.

TABLE 1

| | Numerically calculated FWHM | Experimentally measured FWHM | Rayleigh diffraction limit (The focusing limit) |
|---|---|---|---|
| Conventional FZP lens | 1.24 | 1.37 | 1.28 |
| Optimized SOAL | 0.78 | 0.84 | |

(1) FWHM (0.40λ/NA≈0.57λ≈0.84 mm) is narrow as compared to the conventional FZP lens (0.64λ/NA≈0.91λ≈1.37 mm), (2) the Rayleigh diffraction limit (0.61λ/NA≈0.86λ≈1.28 mm) can be overcome, then obtaining subwavelength focusing (0.40λ/NA≈0.57λ≈0.84 mm). Meanwhile, the optimized SOAL has an extremely narrow acoustic passing region (i.e., micro-slit). In practice, this causes a thermal-viscous loss, resulting in a damping effect. Herein, the narrowest acoustic passing region (~0.29 mm) of the optimized region is larger than a thickness of a thermal ($\delta_{thermal}$~0.21 μm) and viscous ($\delta_{viscous}$~0.56 μm) layer estimated from a simple analysis equation. Thus, the thermal-viscous loss effect can be ignored at 20° C. and 1 atm.

However, in order to achieve a SOAL having side FWHM which is much narrower than the optimized SOAL according to the embodiment of the present invention, a narrower micro slit should be fabricated under proper uncertainty. Since the loss maximized by this narrow micro slit may affect the performance of the SOAL significantly, the optimizing process should take a complete combination model of the thermal and acoustic field into account.

In conclusion, in the embodiment of the present invention, optimized was a subminiature SOAL having the subwavelength focusing function which was capable of focusing incident acoustic energy on the subwavelength region. In order to design the optimal SOAL layout topologically, applied was the reverse design method referred to as topology optimization. As utilizing the reverse design methodology proposed in the embodiment of the present invention, the SOAL was designed, allowing maximizing the focusing performance of acoustic energy in the viewpoint of FWHM.

Further, the embodiment of the present invention proved that the SOAL optimized by experimentally embodying the SOAL overcome the diffraction limit, achieving subwavelength focusing. Meanwhile, for practical diagnosis and treatment processes rather than clinical situation, acoustic energy should be focused on a position far from the acoustic lens (i.e., z>>λ). That is, the acoustic lens should have a long focal length. The optimized SOAL allows focusing acoustic energy on a position being approximately 16λ, thus supplementing the drawback of a short-field imaging approach method including several AMM based Lenses. There is still a problem to be solved in connection with the thermal-viscous loss effect resulted from an extremely narrow micro-slit, however, the optimized SOAL has a great advantage in pragmatic aspect.

Further, the optimized SOAL according to the present invention provides diverse advantages such as low-power therapy, the far-field focus of a long focal length and focal length control through replacement with the optimized SOAL, thus improving therapeutic performance of High Intensity Focused Ultrasound (HIFU)/High Intensity Therapeutic Ultrasound (HITU). Further, in order to achieve an acoustic imaging of super-resolution in practice, the optimized SOAL can be applied to an acoustic microscope. Further, the concept of the optimized SOAL may be extended to a variety of wave (elasticity, sound, light wave) based systems through a similar design program to that proposed in the embodiment of the present invention.

Further, the configuration and method of the embodiments as described above are not restrictively applied to the aforementioned apparatus and method. The whole or part of the respective embodiments may be selectively combined so as to make various modifications of the embodiments.

What is claimed is:

1. A super-oscillatory planar ultra-thin acoustic lens for subwavelength focusing in a megasonic range, the super-oscillatory planar acoustic lens comprising:
   a plurality of concentric regions arranged in a concentric shape with reference to a center point, wherein the concentric regions are formed by crossing acoustic insulation regions for insulating incident acoustic waves and transmission regions for transmitting acoustic waves, in a radial direction from the center point, and focus the incident acoustic wave energy onto a subwavelength region,
   the acoustic lens comprises ring shape apertures, and
   a layout which is a radius of each of the plurality of acoustic insulation regions and transmission regions in the concentric region, is determined by a topology optimization reverse design method and provided being spaced apart from a transducer,
   wherein a layout design of the acoustic insulation region and the transmission region is determined by following formula 2:

$$\max_{re} J_0 = \text{Acoustic Energy}]_{bright} = \qquad \text{[Formula 2]}$$

$$J_{AE}^{bright} = \frac{1}{2 p_{water} c_{water}} \int_{\Omega_{bright}} |p|^2 d\Omega$$

$$\text{subject to } g_1 = \frac{\int_{\Omega_{design}} \gamma_e d\Omega}{(VFF)V_{design}} - 1 \leq 0$$

$$g_2 = \left(\frac{|p|^2_{\partial^2 \Omega_{FWHM}}}{0.5|p|^2_{\partial^2 \Omega_{design}}} - 1\right)^2 \leq \varepsilon$$

$$\gamma_e = [\gamma_1, \gamma_2, \ldots, \gamma_{NE}] \in (0{\sim}1)$$

in the formula 2, p is an acoustic pressure, $\gamma_e$ is a design variable which is varied in an interval of 0 to 1 during phase optimization, VFF is an essential volume ratio which defines a ratio of an opaque region to an entire design domain, $V_{design}$ is a volume of the entire design domain, e is a threshold for relaxation of a constraint ($g_2$), and NE is a sum of design variables.

2. The super-oscillatory planar ultra-thin acoustic lens for subwavelength focusing in a megasonic range according to claim 1, wherein the acoustic lens is composed of a binary ring mask-type super-oscillatory acoustic lens.

3. The super-oscillatory planar ultra-thin acoustic lens for subwavelength focusing in a megasonic range according to claim 2, wherein during topology optimizing process, acoustic energy in a main focusing region is gradually increased, allowing optimization.

4. The super-oscillatory planar ultra-thin acoustic lens for subwavelength focusing in a megasonic range according to claim 3, wherein the acoustic lens is provided being not attached to a transducer but spaced apart therefrom, allowing being replaced with other acoustic lenses having different, various layouts.

5. The super-oscillatory planar ultra-thin acoustic lens for subwavelength focusing in a megasonic range according to claim 4, wherein an FWHM (Full Width at Half Maximum) in the main focusing region is a Rayleigh diffraction limit or under.

6. The super-oscillatory planar ultra-thin acoustic lens for subwavelength focusing in a megasonic range according to claim 5, wherein the FWHM (Full Width at Half Maximum) in the main focusing region is 0.5λ/NA or under.

7. The super-oscillatory planar ultra-thin acoustic lens for subwavelength focusing in a megasonic range according to claim 5, wherein a thickness of the acoustic lens is 0.5λ, or under.

8. The super-oscillatory planar ultra-thin acoustic lens for subwavelength focusing in a megasonic range according to claim 1, wherein according to updated design variables ($\gamma_e$), material distribution in the design domain is determined on the basis of following formula 3a and formula 3b:

$$p(\gamma_e) = \left(\frac{1}{\rho_{water}} + \gamma_e^{q1}\left(\frac{1}{\rho_{SUS303}} - \frac{1}{\rho_{water}}\right)\right)^{-1} \qquad \text{[Formula 3a]}$$

$$c(\gamma_e) = \left(\frac{1}{c_{water}} + \gamma_e^{q1}\left(\frac{1}{c_{SUS303}} - \frac{1}{c_{water}}\right)\right)^{-1} \qquad \text{[Formula 3b]}$$

in the formulas 3a and 3b, $q^1$ and $q^2$ are penalty coefficients for a mass density (ρ) and an acoustic speed (c), respectively.

9. A design method of a super-oscillatory planar ultra-thin acoustic lens for subwavelength focusing in a megasonic range, the design method of the super-oscillatory planar acoustic lens comprising steps of:
   determining a design domain for an optimal layout;
   setting up a desired main focusing region and determining a transmission material and an acoustic insulation material;
   setting up a desired FWHM and adopting a constraint;
   optimizing a layout of the transmission regions and the acoustic insulation region by a topology optimization reverse design method; and
   fabricating an acoustic lens through a photo etching method on the basis of the optimized layout,
   wherein a layout design of the acoustic insulation region and the transmission region is determined by following formula 2:

$$\max_{re} J_0 = \text{Acoustic Energy}]_{bright} = \qquad \text{[Formula 2]}$$

$$J_{AE}^{bright} = \frac{1}{2 p_{water} c_{water}} \int_{\Omega_{bright}} |p|^2 d\Omega$$

$$\text{subject to } g_1 = \frac{\int_{\Omega_{design}} \gamma_e d\Omega}{(VFF)V_{design}} - 1 \leq 0$$

-continued $$g_2 = \left( \frac{|p|^2_{\partial^2 \Omega FWHM}}{0.5|p|_{\partial^2 \Omega design}} - 1 \right)^2 \leq \varepsilon$$

$$\gamma_e = [\gamma_1, \gamma_2, \ldots, \gamma_{NE}] \in (0 \sim 1)$$

in the formula 2, p is an acoustic pressure, $\gamma_e$ is a design variable which is varied in an interval of 0 to 1 during phase optimization, VFF is an essential volume ratio which defines a ratio of an opaque region to an entire design domain, $V_{design}$ is a volume of the entire design domain, e is a threshold for relaxation of a constraint ($g_2$), and NE is a sum of design variables.

10. The design method of a super-oscillatory planar ultra-thin acoustic lens for subwavelength focusing in a megasonic range according to claim 9, wherein during topology optimizing process, acoustic energy is gradually increased in a main focusing region, allowing optimization.

11. The design method of a super-oscillatory planar ultra-thin acoustic lens for subwavelength focusing in a megasonic range according to claim 9, wherein according to updated design variables ($\gamma_e$), material distribution in the design domain is determined on the basis of following formula 3a and formula 3b:

$$p(\gamma_e) = \left( \frac{1}{\rho_{water}} + \gamma_e^{q_1} \left( \frac{1}{\rho_{SUS303}} - \frac{1}{\rho_{water}} \right) \right)^{-1} \quad \text{[Formula 3a]}$$

$$c(\gamma_e) = \left( \frac{1}{c_{water}} + \gamma_e^{q_1} \left( \frac{1}{c_{SUS303}} - \frac{1}{c_{water}} \right) \right)^{-1} \quad \text{[Formula 3b]}$$

in the formulae 3a and 3b, $q^1$ and $q^2$ are penalty coefficients for a mass density ($\rho$) and an acoustic speed (c), respectively.

12. The design method of a super-oscillatory planar ultra-thin acoustic lens for subwavelength focusing in a megasonic range according to claim 11, wherein during optimizing process, the design variables are updated on the basis of slope information calculated by AVM (Adjoint Variable Method).

13. The design method of a super-oscillatory planar ultra-thin acoustic lens for subwavelength focusing in a megasonic range according to claim 12, wherein during the optimizing process, a heaviside projection filtering method having beta-continuation is repeated.

* * * * *